United States Patent [19]

Schmid et al.

[11] Patent Number: 5,173,165

[45] Date of Patent: Dec. 22, 1992

[54] ENZYME ELECTRODE AND THE USE THEREOF

[75] Inventors: Rolf Schmid, Braunschweig, Fed. Rep. of Germany; Juozas Kulys, Vilnius, U.S.S.R.

[73] Assignee: Gesellschaft fur Biotechnologische Forschung mbH (GBF), Braunschweig, Fed. Rep. of Germany

[21] Appl. No.: 595,536

[22] Filed: Oct. 11, 1990

[30] Foreign Application Priority Data

Oct. 13, 1989 [DE] Fed. Rep. of Germany ....... 3934299

[51] Int. Cl.$^5$ ............................................. G01N 27/26
[52] U.S. Cl. ............................... 204/403; 204/153.12; 204/415; 435/817

[58] Field of Search ................... 204/403, 153.12, 415; 435/817, 28, 288

[56] References Cited

U.S. PATENT DOCUMENTS 4,711,245 12/1987 Higgins et al. ....................... 204/403

FOREIGN PATENT DOCUMENTS 221078 9/1981 Fed. Rep. of Germany ...... 435/817

Primary Examiner—John Niebling
Assistant Examiner—Bruce F. Bell
Attorney, Agent, or Firm—Kane, Dalsimer, Sullivan, Kurucz, Levy, Eisele and Richard

[57] ABSTRACT

The invention relates to an enzyme electrode having a bienzyme system containing fungal peroxidase or horseradish peroxidase and one or more oxidases, and to the use of the electrode.

9 Claims, 12 Drawing Sheets

ENZYME ELECTRODE AND THE USE THEREOF

BACKGROUND OF THE INVENTION

1. Field of the Invention

A bienzyme electrode contains a peroxidase and an oxidase. It is generally useful in bioelectrochemical assays, for example for determining the substrates of ethanol oxidase, choline oxidase, cholesterol oxidase or a D-amino-acid oxidase.

2. Brief Description of the Related Art

Enzyme electrodes have gained considerable importance with regard to determinations of metabolites in medicine, biotechnology, food technology and many other areas of science and technology; Schmide, R. D. et al. (1988). Biosensors and "Bioelectronics". In Biotechnology (ed. H. -J. Rehm, G. Reed) VCH Verlagsgesellschaft, Wein, 6b, 317. Bienzyme systems which contain peroxidases and oxidases have been used for the manufacture of highly selective amperometric enzyme electrodes; Kulys, J. J. et al. (1981). Biolectrochem. Bioenerg., 8, 81–88. Ferrocyanide was used as soluble mediator. These electrodes were not suitable for use in vivo or for monitoring bioreactors. Other systems which contained organometallic compounds and peroxidase/oxidase did not need a mediator but the efficiency of the peroxidase activity was low, and the electrodes exhibited a delayed response and insufficient stability.

We have proposed the use of a peroxidase from the fungus Arthromyces ramosus; Shinmen, Y. et al. (1986). Agric. Biol. Chem., 50, 247–249; or of chemically modified electrodes; Cenas, N. K. et al. (1981). Biocelectrochem. Bionerg., 8, 103–113, in order to increase the efficiency of the peroxidase activity and produce a bienzyme electrode without mediator. To our knowledge no fungal peroxidase has previously been used to manufacture an electrochemical system even though, depending on the substrate used, it has shown a catalytic activity which is 2.9 to 540 times higher than horseradish peroxidase; Brochure: neue Peroxidase aus dem Pilz Arthromyces ramosus (Novel Peroxidase from the fungus Arthromyces ramosus). Suntory Ltd. Institute for Fundamental Research Mishima-gun, Osaka 618 Japan.

Chemical modifications have been widely used in the manufacture of enzyme electrodes; Aston, W. J. (1987), Biosensors Fundamentals and Application (Ed. A. P. F. Turner, I. Karube, G. S. Wilson), Oxford University Press, Oxford, New York, Tokyo, 276–291. The first chemically modified electrode contained tetracyanoquinodimethane and the potassium salt thereof Cenase et al., supra. Unfortunately some oxidases, such as, for example, choline oxidase, cholesterol oxidase, amino-acid oxidase and D-amino-acid oxidase do not react with modifying substances; Davis, G. (1977). Biosensors Fundamentals and Application (Ed. A. P. F. Turner, I. Karube, G. S. Wilson), Oxford University Press, Oxford, New York, Tokyo, 247–257 so that it is impossible to construct an electrode which simply contains only oxidase.

SUMMARY OF THE INVENTION

According to one embodiment, the invention thus relates to an enzyme electrode with a bienzyme system which is characterized by fungal peroxidase and one or more oxidases as well as the absence of mediator.

According to a further embodiment, the invention relates to an enzyme electrode with a bienzyme system which is characterized by horseradish peroxidase, one or more oxidases and a water-insoluble mediator.

Water-insoluble mediators are, for example, dimethylferrocene and tetrathiafulvalene. The oxidases can be glucose oxidase, alcohol oxidase, choline oxidase, D-amino-acid oxidase and/or cholesterol oxidase.

According to specific embodiments (a) the peroxidase and the oxidase(s) can be immobilized on the electrode or (b) the peroxidase can be immobilized on the electrode, and the oxidase(s) can be kept in a space, for example in an annular gap, which is formed by the electrode together with a semipermeable membrane, or (c) both the peroxidase and the oxidase(s) can be kept in a space, for example in an annular gap, which is formed by the electrode together with a semipermeable membrane.

In this connection the peroxidase and optionally the oxidase(s) can be covalently bonded to the electrode, for example with the aid of carbodiimide or glutaraldehyde.

The conductive electrode material can be graphite or a material containing graphite.

The enzyme electrode according to the invention can be designed in the form of a strip, the electrode possibly being arranged on a flat support, optionally together with a counterelectrode.

The enzyme electrode according to the invention is suitable for determining oxidase substrates or for determining enzyme activity.

BRIEF DESCRIPTION OF THE FIGURES

Further characteristics of the invention are described with reference to the attached figures.

Figure 9:
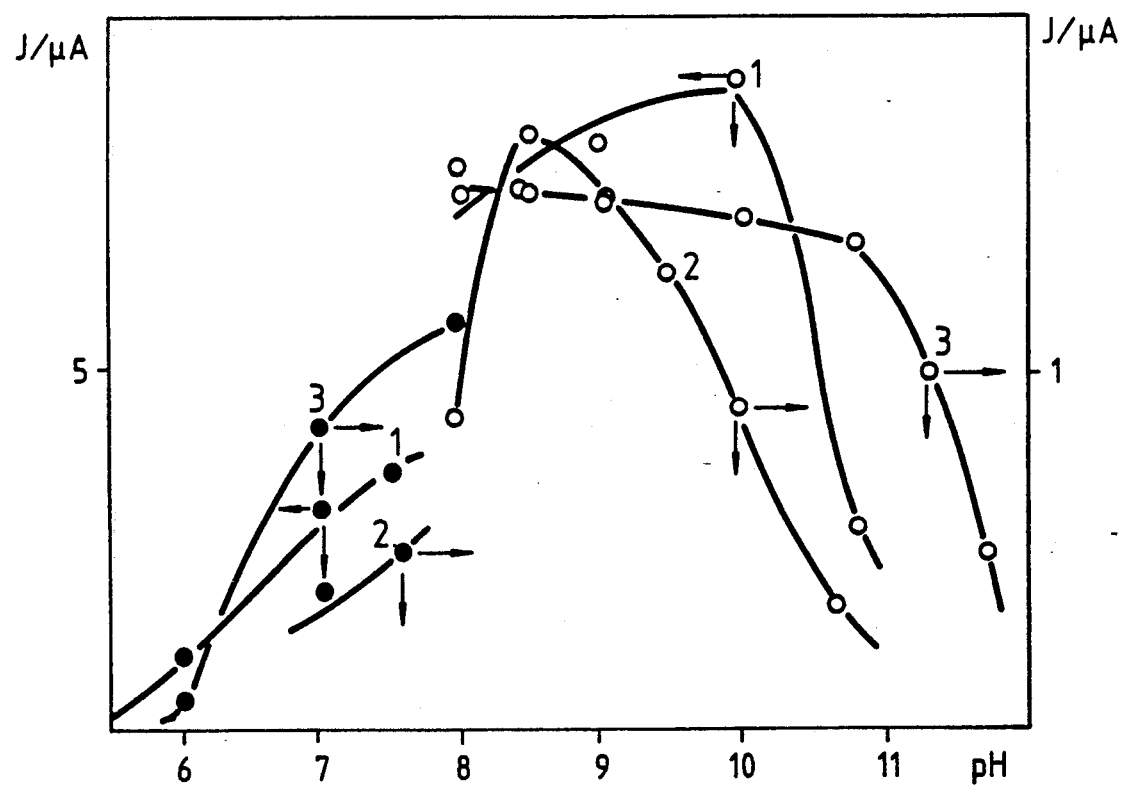

FIG. 9 shows the steady state current plotted against the pH of a HRP/AO (1), of a HRP/D-AAO (2) and of a HRP/ChO electrode (3). Phosphate buffer (dots), glycine buffer (circles). Electrode potential 20 mV (1) and 0 mV (2,3), concentrations: methanol 0.33 mM (1), D-alanine 0.069 mM (2), choline chloride 0.061 mM (3), modifying substance DMFc (1-3).

Figure 10:
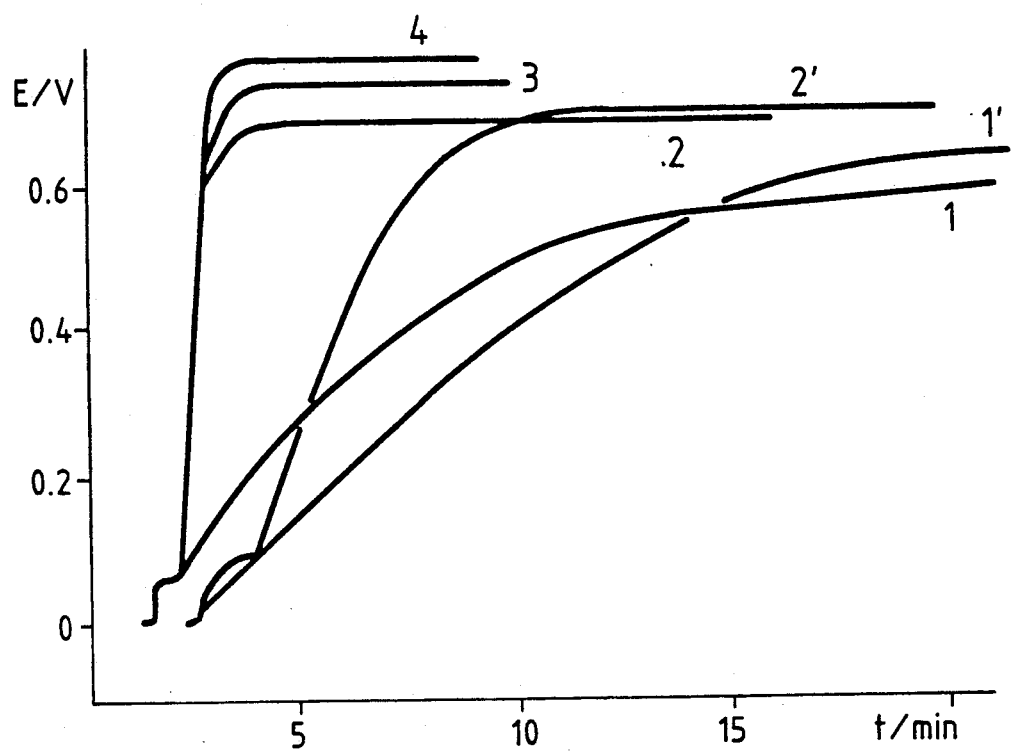

FIG. 10 shows a plot of the time-course of the electrode potential of an ARP/GO (1', 2') and of an ARP electrode (1-4), pH 7.0 (1, 2), 6.01 (1', 2', 3), 4.92 (4), concentrations: $H_2O_2$ 1.3 $\mu$M (1), 0.32 mM (2-4), glucose 0.6 mM (1'), 1.8 mM (2').

Figure 11:
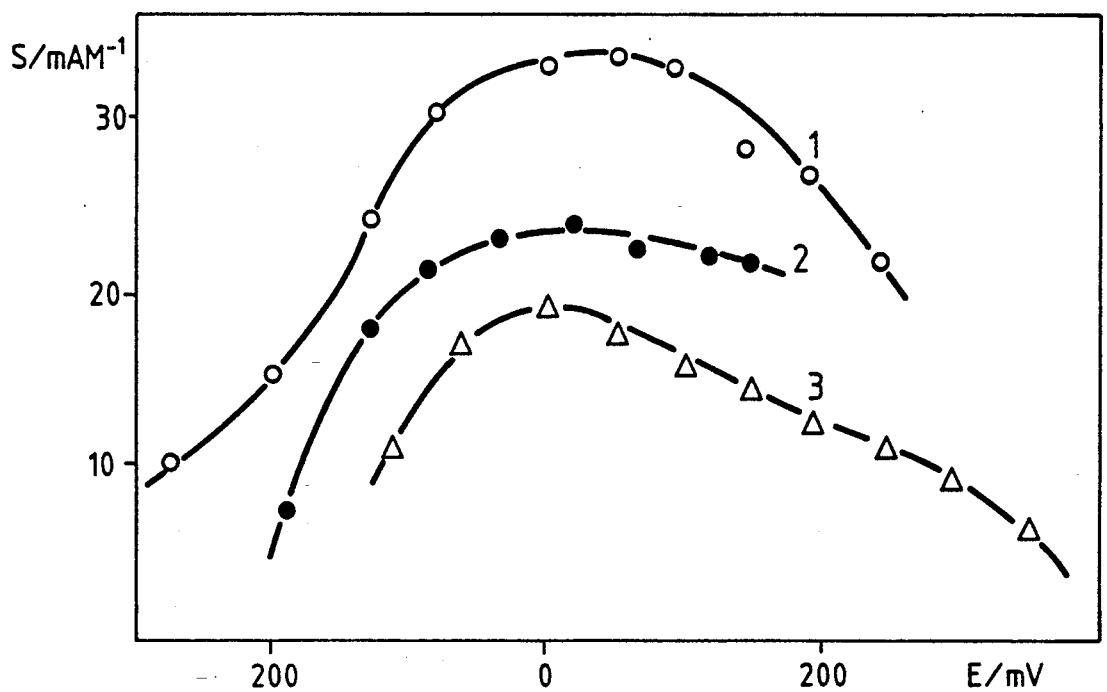

FIG. 11 shows the HRP/AO electrode sensitivity for methanol plotted against the electrode potential at pH 7.0; modifying substances: TTF (1), DMFc (2), TCNQ (3).

Figure 12:
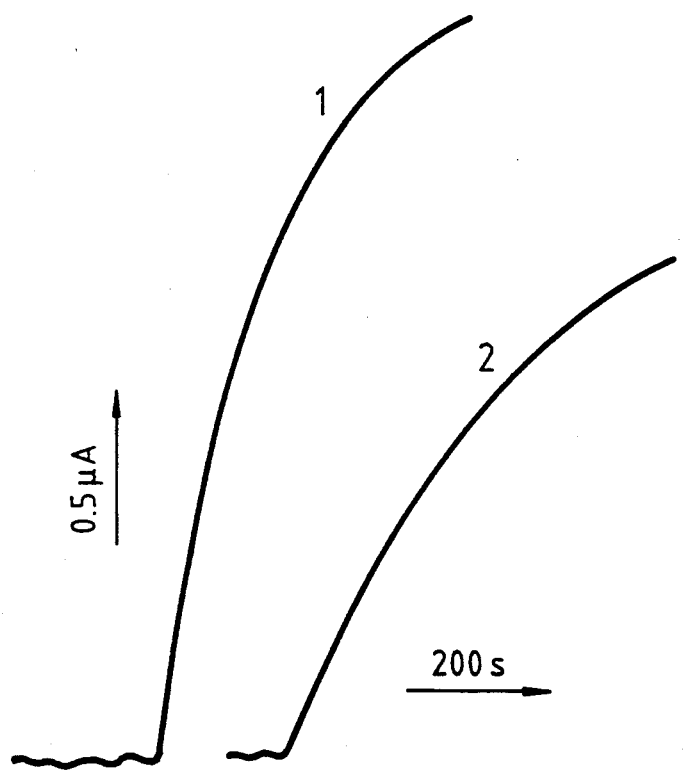

FIG. 12 shows a plot of the time-course of the HRP/D-AAO electrode cathode current related to the race-mase activity (5.5 U (1) and 2.1 U (2)).

Figure 13:
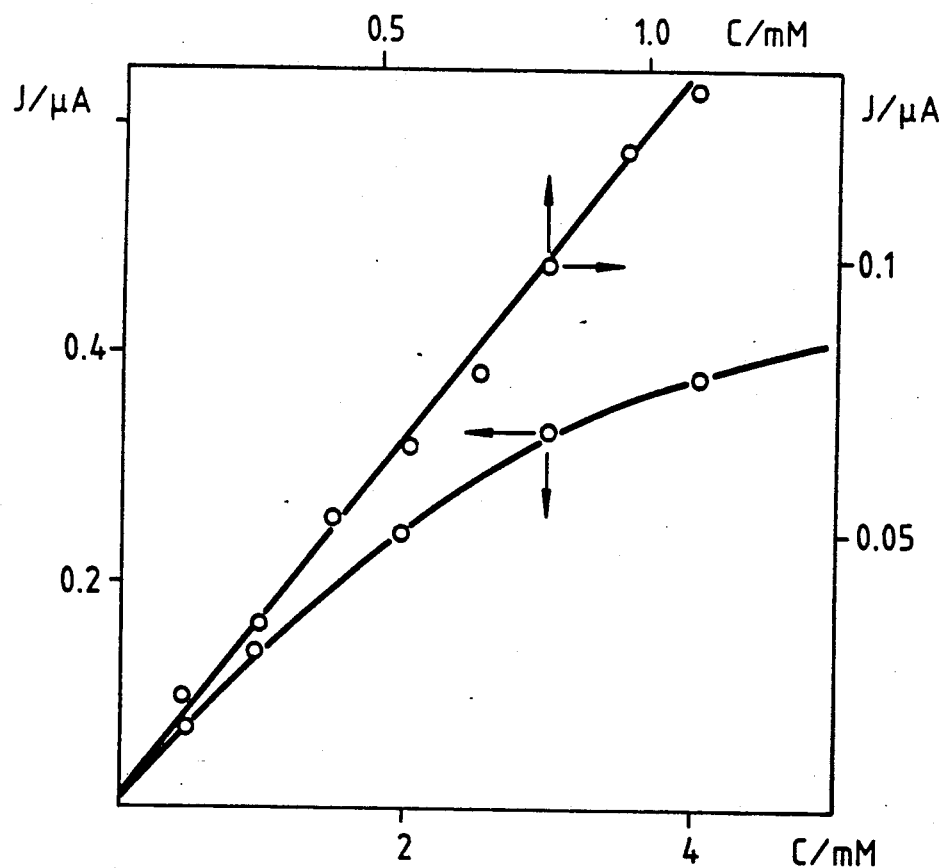

FIG. 13 shows a plot of the calibration curve of the steady state current against the ethanol concentration of a electrochemical HRP/AO strip at pH 9.0, modifying substance DMFc, potential −10 mV.

DETAILED DESCRIPTION OF THE PREFERRED EMBODIMENTS OF THE INVENTION

Manufacture of the electrodes

Figure 1:
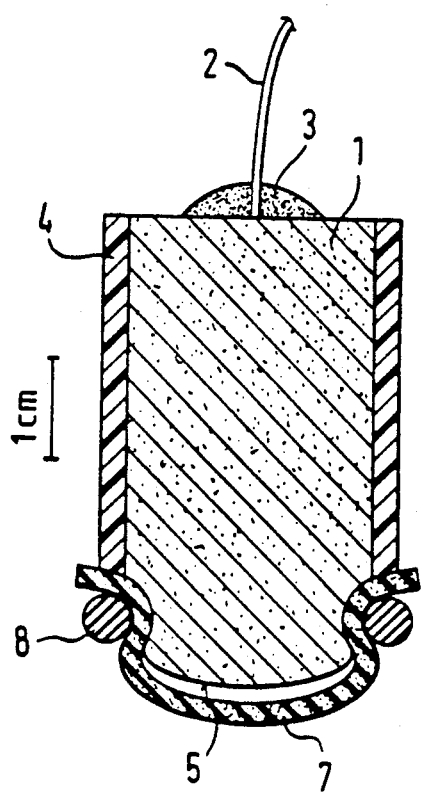
FIG. 1 and FIG. 14 show diagrammatically side views of the cross-section through an electrode.
Figure 14:
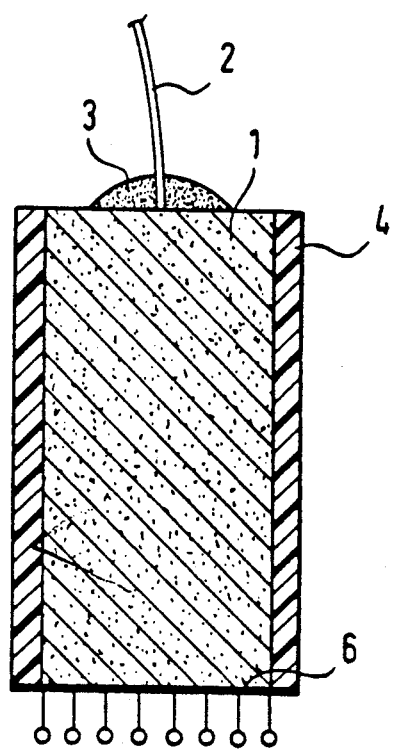

A) As shown in FIG. 1, and FIG. 14, an enzyme electrode contains graphite rods (1) (diameter 10 mm, Ringsdorff-Werke GmbH). In each case a copper wire (2) was stuck to the ends of the rods (30 mm long) using epoxy/silver (3). The sides of the electrodes were insulated with a polyethylene film (4). The other end of the electrodes was rubbed with emery paper (220 $\mu$m) in order to give it a spherical shape (radius 40 mm) (5) or flat shape (6).

B) Subsequent to the pretreatment with emery paper, the electrode shown in FIG. 14 (flat shape) was activated at room temperature using 5×50 $\mu$l of water-soluble carbodiimide (N-(3-dimethylaminoprop-yl)-N'-ethylcarbodiimide hydrochloride) in 0.1 M K phosphate solution of pH 4.5 (20 mg/ml). After 0.5 h, the electrode was washed with the same solution. Then 20 $\mu$l of fungal peroxidase (10 mg/ml) and glucose oxidase (20 mg/ml) were applied dropwise to the electrode. After 0.5 h, the electrode was washed with phosphate buffer (pH 7.0) and stored in this buffer in a refrigerator.

The fungal peroxidase/alcohol oxidase electrode was manufactured using double immobilization. After the fungal peroxidase had been immobilized as described above, the electrode was washed with phosphate buffer (pH 7.0). 20 $\mu$l of alcohol oxidase solution (5 mg/ml) in phosphate buffer which contained 2.5% glutaraldehyde were now applied dropwise to the electrode and dried in the air. The electrode was washed with the above buffer and stored in a refrigerator.

In the case of fungal peroxidase/choline oxidase electrodes, 20 $\mu$l of choline oxidase (5 mg/ml) in phosphate buffer (pH 7.0) were trapped with a dialysis membrane (25 $\mu$m) (7) on the spherical end of the graphite electrode on which fungal peroxidase had been covalently immobilized as described above. The membrane was held in position by a rubber band (8). The electrode was stored in phosphate buffer (pH 7.0) in a refrigerator.

C) Horseradish peroxidase-containing electrodes were manufactured in the following way: after pretreatment with emery paper the graphite surface was washed twice with 50 $\mu$l of toluene and dried in the air. Subsequently 20 $\mu$l of the mediator solution (10 mg/ml) in toluene were applied dropwise to the electrode and evaporated. This step was repeated twice. After 0.5 h, 20 $\mu$l of enzyme solution (20 mg/ml peroxidase and 5 mg/ml oxidase) in 0.1 M K phosphate buffer (pH 7.0) were trapped with a dialysis membrane (25 $\mu$m) (7) which was held by a rubber band (8). Oxidases which were used were alcohol oxidase, choline oxidase and D-amino-acid oxidase.

In addition another electrode type was manufactured by dissolving peroxidase (1 mg) and alcohol oxidase (5 mg) in 0.1 M K phosphate buffer (pH 7.1) which contained 2.5% glutaraldehyde. 20 $\mu$l of this solution were applied dropwise to the electrode and dried. After 1.5 h, the electrode was washed with 0.1 M K phosphate buffer (pH 7.0). In the case of the cholesterol oxidase electrode, 20 $\mu$l of peroxidase solution (10 mg/ml) were trapped as described above. Cholesterol oxidase was used in the soluble form.

D) Electrochemical strips (FIG. 2) were manufactured from cellulose acetate (0.5 mm) (1). Two carbon film electrodes (1 mm) (3, 4) were stuck on using silicone rubber adhesive. One electrode (3) had previously been covered with Ag from KAgCN solution (1%), another one (4) was treated with a mediator, and horseradish peroxidase and alcohol oxidase were immobilized as described above. The strips were stored in the air in a dry place.

Measurements

Figure 2:
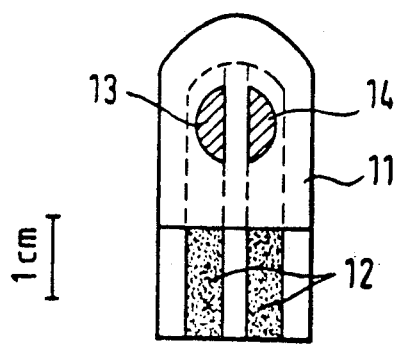
FIG. 2 is a diagrammatic side view of the cross-section of an electrochemical strip.

The electrode currents were measured at room temperature in a standardized three-electrode circuit using 15 ml of buffer. All potentials were determined with a KCl-saturated Ag/AgCl electrode as reference. Used to determine the cholesterol concentration were 4 ml of phosphate solution (pH 7.0) which contained 0.4% Thesit and to which 0.37 U of cholesterol oxidase in 40 $\mu$l of the same buffer had been added. The enzyme electrode was switched off for 10 min and then switched on again, during which the current was recorded. The damping time of the potentiostate was 4 s. The current strength of the electrochemical strip was measured in a two-electrode circuit. Before the start of the measurements, substrate solution (20–50 $\mu$l) was applied dropwise to the electrodes (3, 4) (FIG. 2). After connecting the graphite film contacts (2) to a potentiostat, the current was measured.

Reagents and Buffer Solutions

Horseradish peroxidase (HRP) (E.C. 1.11.1.7) (198.8 U/mg) grade II, Boehringer Mannheim GmbH.

Fungal peroxidase (ARP) (E.C. 1.11.1.7) (Arthromyces ramosus, 2110 U/mg) Suntory Ltd.

Alcohol oxidase (AO) (E.C. 1.1.3.13) (Candida boldini, 8.1 U/mg) Boehringer Mannheim GmbH.

Choline oxidase (ChO) (E.C. 1.1.3.17) (Alcaligenes species, 11 U/mg) Sigma

D-Amino-acid oxidase (D-AAO) (E.C. 1.4.3.3) (pig kidney, 14 U/mg) Sigma.

Cholesterol oxidase (ChlO) (E.C. 1.1.3.6) (Pseudomonas species, 40 U/mg) Sigma.

L-Alanine racemase (L-AR) (B. stearothermophilus) GBF.

Tetracyanoquinodimethane (TCNQ)—Polysciences Inc.; 1,1'-dimethylferrocene (DMFc)—Aldrich; Tetrathiafulvalene (TTF)—Aldrich; D-alanine—Serva; choline chloride, D-serine, D-aspartic acid, D-lysine, L-valine, cholesterol - Sigma; Thesit - Boehinger Mannheim GmbH; N-(3-dimethylaminopropyl)-N'-ethylcarbodiimide hydrochloride—Fluka.

Miscellaneous reagents—Merck.

Buffers used: 0.1 M acetate (pH 4.5-5.5), 0.1 M K phosphate (pH 5.5-8.0) and 0.1 M glycine (pH 8-11.7).

Glucose solutions were stored overnight in order to ensure that the equilibrium of the alpha and beta anomers was established. The ethanol solutions for the calibration of the strips contained 0.1 M KCl.

Response Time of the Enzyme Electrode and Calibration

Figure 3:
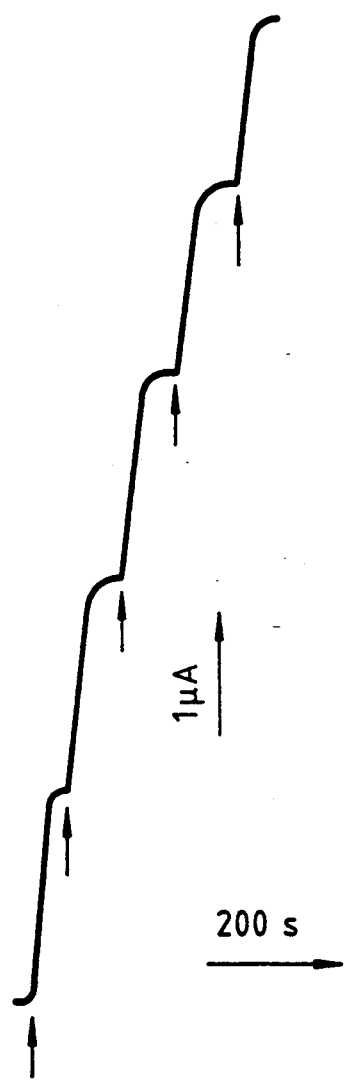
FIG. 3 shows a plot of the time-course of the cathode current of an ARP/GO electrode generated at pH 6.01. Electrode potential 130 mV. The arrows indicate an injection of 0.6 mM D-glucose.
Figure 4:
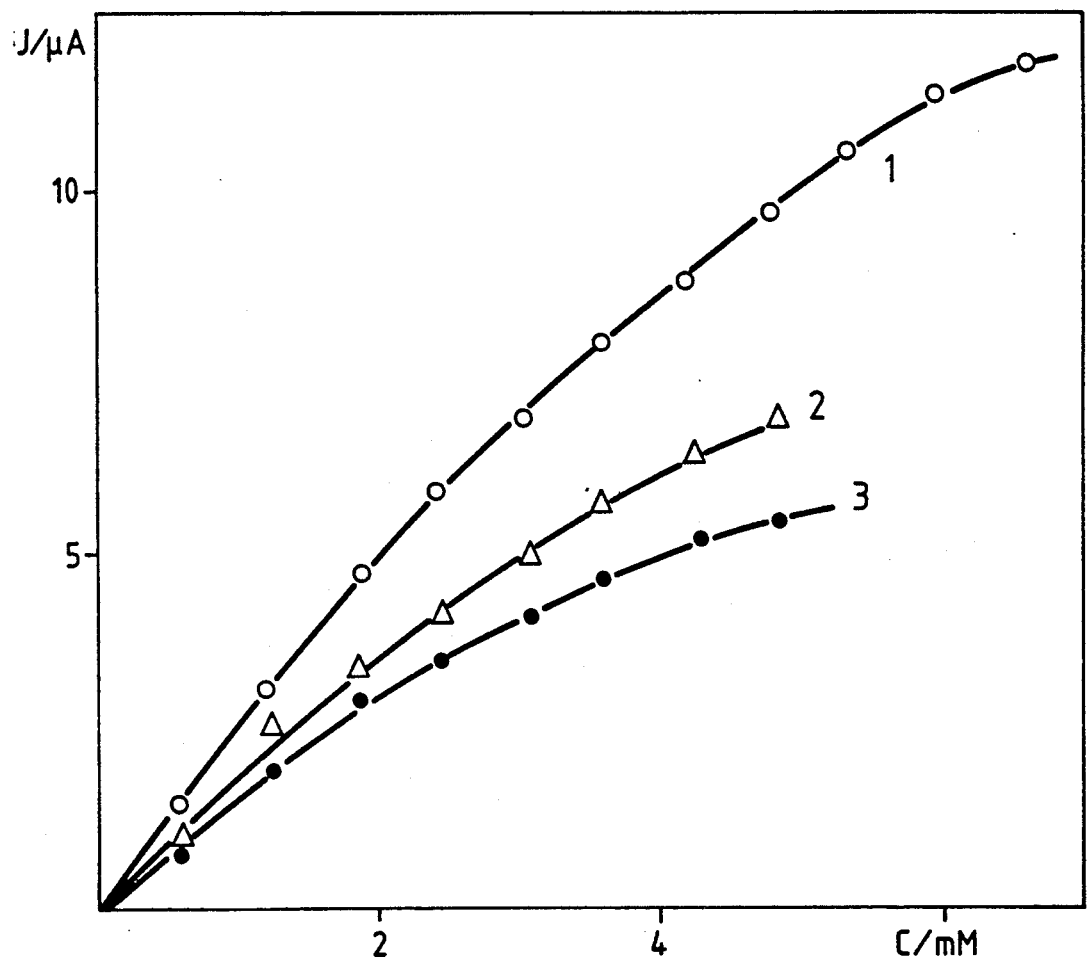
FIG. 4 shows a plot of the calibration curve of the steady state current against the glucose concentration of an ARP/GO electrode at pH 6.01. Electrode potential 130 mV (1), 530 mV (2) and 630 mV (3).

The baseline current of the ARP/GO electrode in phosphate buffer (pH 6.01) was negligibly small with an electrode potential of 130 mV. On addition of the glucose solution the cathode current increased. The response time (90% of the steady state current) was 12 s (FIG. 3). In the concentration range from 0.5 to 6.5 mM glucose, a hyperbolic calibration curve resulted, $I_{max}=33$ μA and $K_m(app)=12.5$ mM (FIG. 4). When the electrode potential was increased, the maximum current was reduced but $K_m(app)$ did not change greatly. With an electrode potential of 530 and 630 mV, $K_m(app)$ was about 11.1 and 9.8 mM, respectively. The sensitivity of the electrode in a concentration range up to 2 mM glucose was 2.6 mA/M (E=130 mV), 1.9 mA/M (E=530 mV) and 1.6 mA/M (E=630 mV).

The bienzyme ARP/AO electrode generated a cathode current on addition of methanol to the buffer. The response time of this electrode which contained doubly immobilized enzymes was increased to as much as 30 s. Up to a concentration of 0.7 mM methanol, there was a linear relation between electrode current and substrate used (pH 7.0). The sensitivity of the electrode was 0.6 mA/M (E=30 mV).

The response time of the bienzyme ARP/ChO electrode was increased to as much as 40 s. This electrode showed a linear calibration plot up to 2.5 mM choline chloride (pH 7.0). The electrode sensitivity was 0.48 mA/M (E=70 mV).

Figure 5:
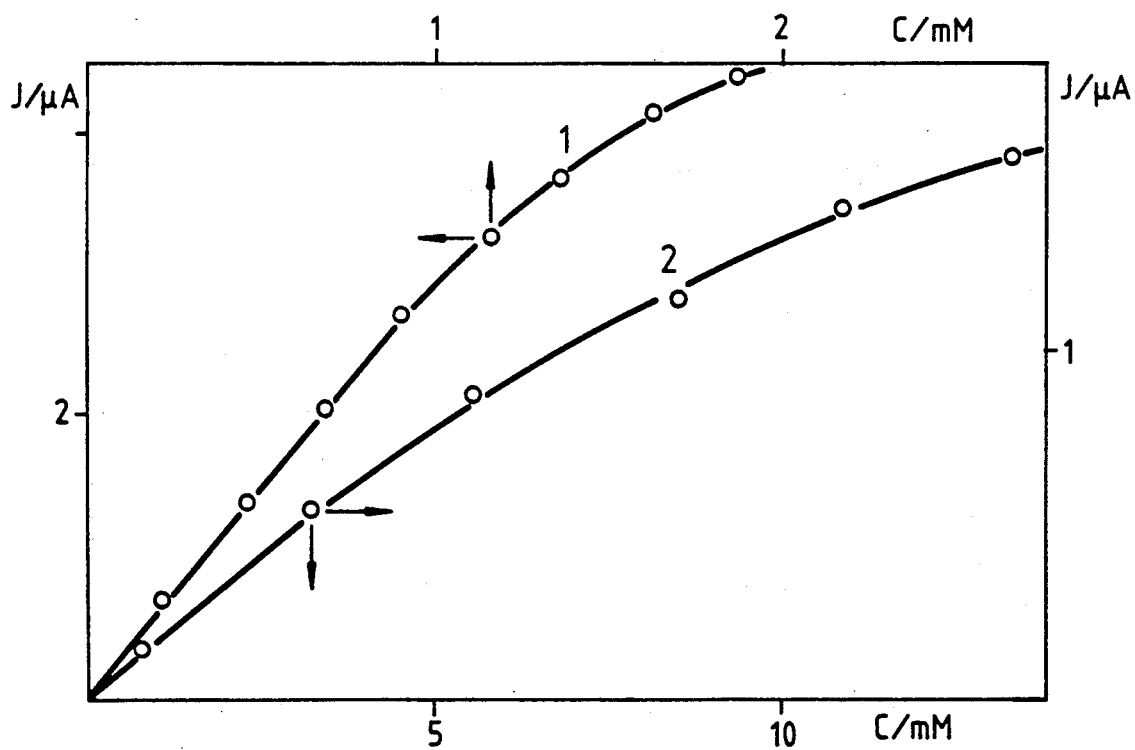
FIG. 5 shows a plot of the calibration curve of the steady state current against the ethanol concentration of a HRP/AO electrode at pH 7.0. Electrode potential 0 mV, modifying substance DMFc. Electrode with trapped (1) and immobilized (2) enzymes.

The baseline current of the HRP/AO electrode which was based on DMFc-modified graphite was negligibly small at −30 mV (pH 7.0). Such an electrode showed a response time of 40 s when the enzymes were trapped in a dialysis membrane. The calibration plot was linear up to a methanol concentration of 1.0 mM (FIG. 5). In contrast, the electrode based on immobilized enzymes showed a hyperbolic calibration curve; $K_m(app)$ was 14.3 mM (FIG. 5). The response time of this electrode was 30 s.

Figure 6:
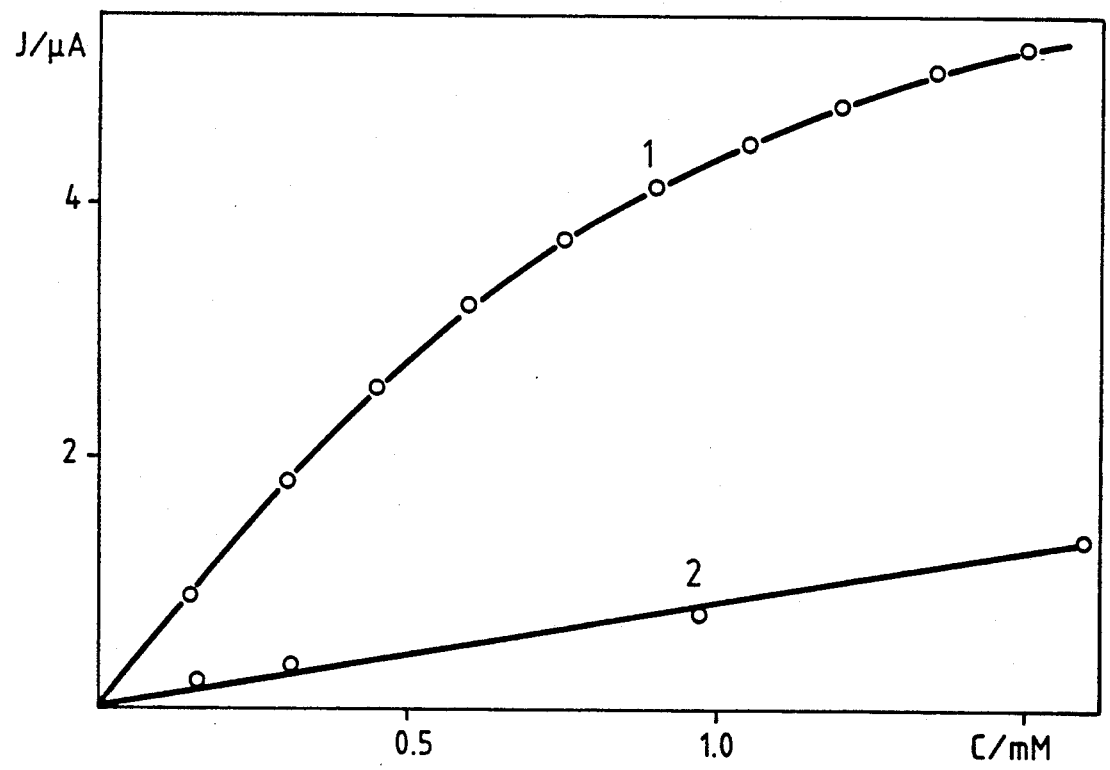
FIG. 6 shows a plot of the calibration curve of the steady state current against the ethanol concentration of a HRP/AO electrode at pH 7.0. Electrode potential −40 mV, modifying substance TTF. First (1) and second (2) day of operation.
Figure 7:
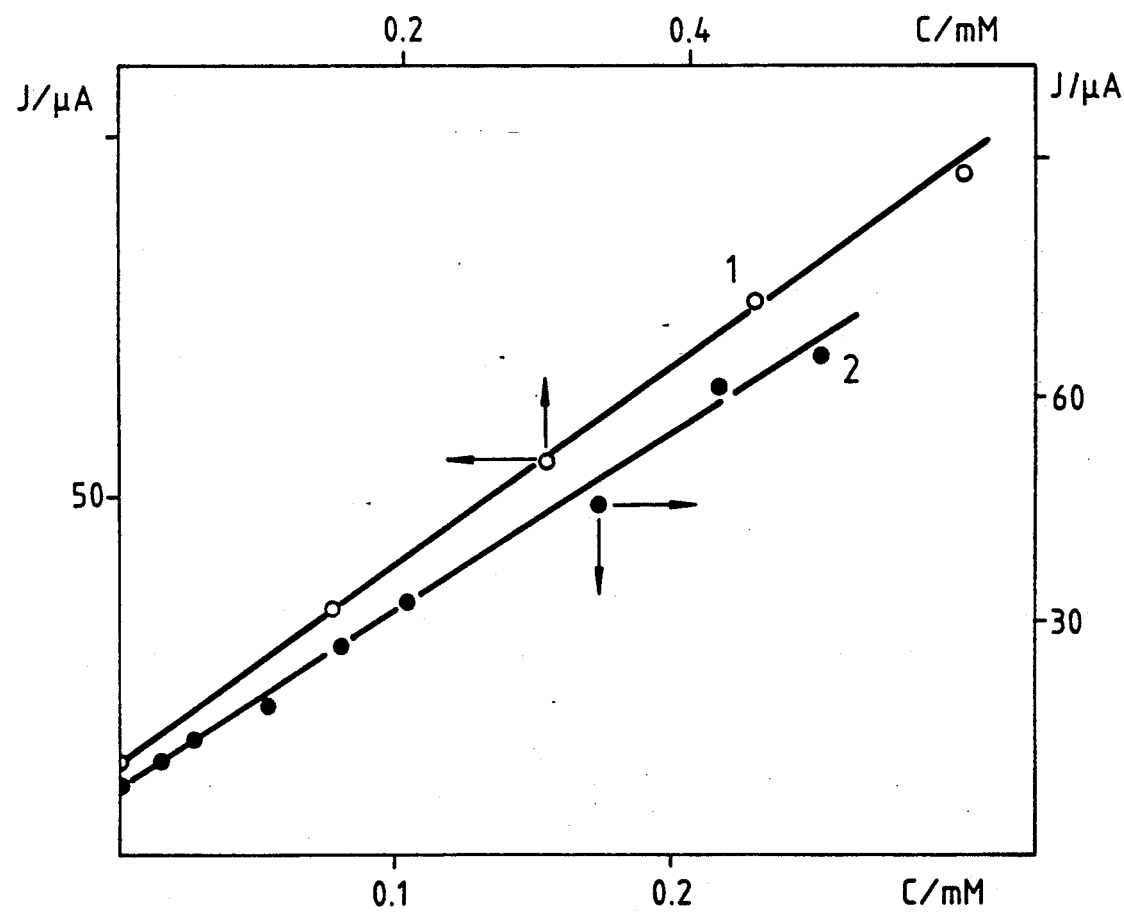
FIG. 7 shows a plot of the calibration curve of the peak current against the ethanol (1) and cholesterol concentration (2) of a HRP/AO (1) and of a HRP/ChlO electrode (2) at pH 7.0 (1,2). 0.4% Thesit (2), electrode potential −40 mV (1) and 20 mV (2), preliminary concentration time 3.6 min (1) and 10 min (2), modifying substance TTF.

The calibration curve of the TTF-HRP/AO electrodes was similar to those of the DMFc-modified systems (FIG. 6). When the switched-off HRP/AO electrode was immersed in the ethanol solution and was switched on 3.6 min later, the peak current was 25 times higher than the steady state current, and it was linear up to an ethanol concentration of 0.6 mM (FIG. 7).

The calibration curves of the TCNQ-modified HRP/AO electrodes were very similar to those of the DMFc- and TTF-modified systems. A comparison of the parameters of the HRP/AO electrodes is shown in Table 1:

TABLE 1

Parameters of the HRP/AO electrodes

| Enzyme | Modifying Substance | pH | E (mV) | Substrate | Measurement range in mM | Enzyme immobilization |
|---|---|---|---|---|---|---|
| Alcohol oxidase, peroxidase | DMFc | 7.0 | 0 | Ethanol | 0.2-1.0 | trapped |
| Alcohol oxidase, peroxidase | DMFc | 7.0 | 0 | Ethanol | 0.8-9.0 | covalently bonded |
| Alcohol oxidase, peroxidase | TTF | 7.0 | −40 | Ethanol | 0.12-0.80 | trapped |
| Alcohol oxidase, peroxidase | TTF | 7.0 | −130 | Methanol | 0.20-0.60 | trapped |
| Alcohol oxidase, peroxidase | TCNQ | 7.0 | 0 | Methanol | 0.20-0.60 | trapped |
| D-Amino acid oxidase, peroxidase | TTF | 7.5 | −10 | D-Valine | 0.008-0.20 | trapped |
| D-Amino acid oxidase, peroxidase | DMFc | 8.0 | 0 | D Alanine | 0.01-0.14 | trapped |
| Choline oxidase, peroxidase | DMFc | 8.5 | 20 | Choline chloride | 0.06-0.3 | trapped |
| Peroxidase (soluble cholesterol oxidase) | TTF | 7.0 | 20 | Cholesterol | 0.013-0.26 | trapped |

The bienzyme HRP/D-AAO electrode exhibited a linear calibration plot up to a concentration of 0.2 mM D-valine. The measurement range of this substance was 8-200 μM (Tab. 1).

The calibration plot of the bienzyme HRP/ChO electrode was linear up to a concentration of 0.3 mM choline chloride. The measurement range was 0.06–0.3 mM (Tab. 1).

A HRP/ChlO bienzyme electrode whose enzymes were trapped or covalently bonded did show a reaction to hydrogen peroxide but no response to cholesterol. For this reason a soluble cholesterol oxidase was used for the cholesterol determination. Subsequent to the biocatalytic preliminary concentration time, the electrode was uncovered in order to increase the electrode current and also to measure ethanol (FIG. 7). During the preliminary concentration period of 10 min, a linear relationship between maximum current and the cholesterol concentration was found up to a concentration of 126 mM (FIG. 7).

PH Dependence of the Enzyme Electrode Current

Figure 8:
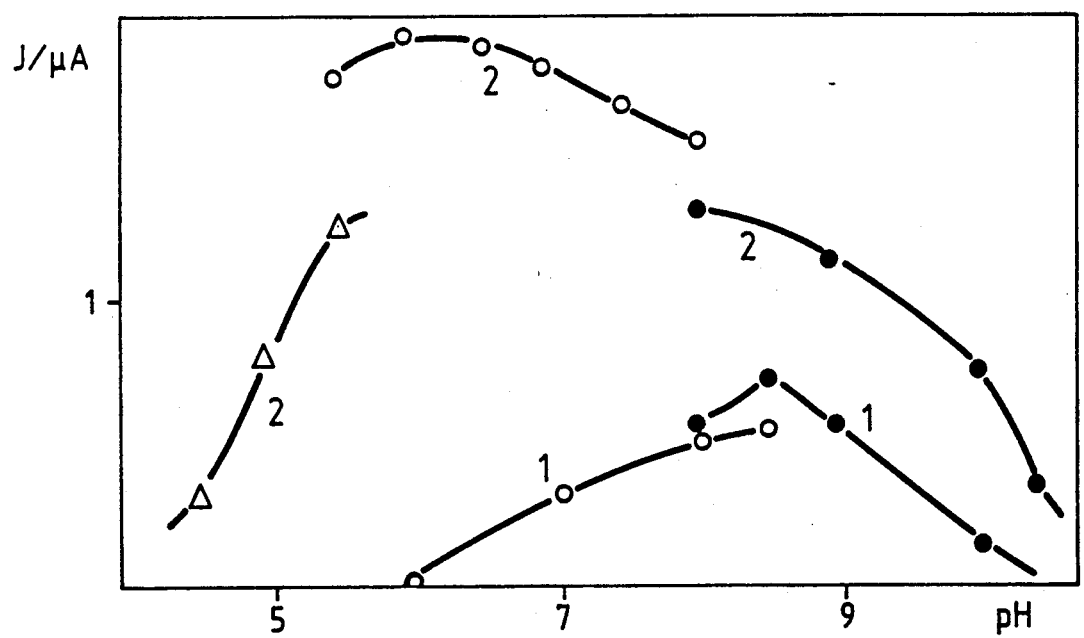
FIG. 8 shows the steady state current plotted against the pH of an ARP/ChO (1) and of an ARP/GO electrode (2), acetate buffer (triangles), phosphate buffer (circles), glycine buffer (dots). Electrode potential 70 mV (1) and 20 mV (2), concentrations: choline chloride 0.08 mM (1) and glucose 0.6 mM (2).

The bienzyme ARP/GO electrode displayed a cathode current in the pH range of 4.5–10.5 (FIG. 8). The highest activity was exhibited by the electrode here in the pH interval between 5.5 and 8.0 in phosphate buffer. However glycine or acetate did not substantially reduce the current.

The pH optimum of the ARP/ChO electrode was at pH 8.7 (FIG. 8). It follows that the activity was higher in glycine buffer.

The HRP/AO electrodes exhibited a pH dependence of the electrode sensitivity in a wide range (FIG. 9). The electrode with the highest activity had its optimum at pH 10. The activity was higher by 75% in glycine buffer than in K phosphate buffer.

The HRP/D-AAO electrode displayed the highest activity at pH 8.5 (FIG. 9). It was higher in glycine buffer than in K phosphate buffer.

The pH-dependent range of the HRP/ChO electrode activity was, in comparison with the HRP/AO or HRP/D-AAO electrodes, shifted in the alkaline direction (FIG. 9). The signal response was once again higher in glycine buffer than in phosphate solutions.

Dependence on Potential of the Enzyme Electrodes

Exactly like the monoenzyme ARP electrodes, the bienzyme ARP/GO electrode formed the same positive potential (FIG. 10). The steady state potential of the ARP/GO electrode was 691 mV and 726 mV at pH 6.01 when 0.6 mM and 1.8 mM glucose, respectively, were used. At high $H_2O_2$ concentrations the steady state potentials of the ARP electrode were 682 mV (pH 7.0), 732 mV (pH 6.01) and 769 mV (pH 4.92). Because of the high potential, the sensitivity of the bienzyme electrode, exactly like that of the monoenzyme ARP electrode, did not change greatly when the electrode potential was increased from 130 mV to 630 mV (FIG. 4).

The dependence of the HRP/AO electrode sensitivity on the electrode potential is shown in FIG. 11. Those electrodes which operate with modified graphite were the most sensitive in the range around 0.0 V. However, in this instance there was a difference in the potential at which the basic current was lowest. With TTF electrodes this was the case at about −130 mV, with DMFc-modified electrodes the value is around −30 mV and with TCNQ-modification around −60 mV. With higher voltages, the basic current of the TTF- and DMFc-modified electrodes increases and the sensitivity decreases. In the case of the TCNQ-modified electrodes, the baseline current remained approximately constant with positive values of the potential but the sensitivity decreased. It is true for all the modified electrodes that the baseline current increased and the sensitivity diminished when the values of the potential were smaller than the "zero basic current potentials".

Specificity of the Enzyme Electrodes

The HRP/AO and HRP/D-AAO electrodes exhibited a large degree of substrate specificity (Tab. 2):

TABLE 2

Specificity of the HRP/AO and HRP/D-AAO electrodes

| Alcohol sensitivity[1] | | D-Amino-acid sensitivity[2] | |
| --- | --- | --- | --- |
| Substrate | Relative sensitivity in % | Substrate | Relative sensitivity in % |
| Methanol | 100 | D-Valine | 100 |
| Ethanol | 28.3 | D-Alanine | 93 |
| 1-Propanol | 12.5 | D-Serine | 20 |
| 2-Propanol | <1 | D-Aspartic acid | <1 |
| | | D-Lysine | |
| | | L-Valine | |
| | | L-Alanine | |
| Measuring conditions: | | pH 7.0, E = −40 mV, 0.1M K phosphate buffer, TTF-modified electrode (1). | |
| | | pH 7.5, E = −10 mV, 0.1M K phosphate buffer, TTF-modified electrode (2). | |

The HRP/AO electrode gave a signal both to 1-propanol and to methanol and ethanol. Methanol was most effective and there was no response of the electrode with 2-propanol. The HRP/D-AAO electrode reacted to D-valine and other hydrophobic D-amino acids (Tab. 2). When L-alanine was converted by alanine racemase, the electrode signal increased; this fact was used to determine the racemase activity (FIG. 12).

Stability of the Enzyme Electrodes

The tested electrodes showed a varying long-term stability. The activity of the ARP/GO electrodes decreases by about 12–15% each day (with a daily measuring time of up to 3 h), and the activity remaining after 7 days was 30–40% of the initial activity. In the case of the ARP/AO electrode the average loss of activity was 35% after operation for 2 h. On the next day we found only 5–7% of the initial activity, while the measured signal to $H_2O_2$ decreased by only 16%. It was possible to observe the same stability for the HRP/AO electrode (FIG. 6). The ARP/ChO electrode proved to be more stable and maintained its efficiency for 2–3 days. During this time the response to $H_2O_2$ decreased to 60%.

The long-term stability of the tested electrodes was mainly determined by the stability of the immobilized oxidase since inactive electrodes without oxidase actively exhibited an initial response to hydrogen peroxide.

The GPO-containing electrodes proved to be the most stable. This is consistent with the high stability of the native enzyme. ChO and AO were less stable. At least as regards the latter enzyme, the other methods of immobilization can be used for its stabilization.

Calibration of the Electrochemical Strip

A bienzyme electrode was used as basis for the manufacture of an electrochemical strip (FIG. 2). The calibration plot of the HRP/AO strip was linear up to an ethanol concentration of 1 mM (FIG. 13). Saturation was detectable at ethanol concentrations >2 mM.

Explanation of the Functioning of a Bienzyme Electrode

Both the electrodes based on ARP alone and those based on ARP and oxidase generate a cathode current. The steady state potential of the ARP and ARP/GO electrodes was extremely high. At the same pH (6.01) it is virtually identical for the ARP electrode ($H_2O_2$ effect) and for the ARP/GO electrode (glucose effect). The results mentioned lead to the conclusion that the electrode potential is determined by the peroxidase effect. In bienzyme electrodes hydrogen peroxide is formed in the presence of the oxidase:

$$S + O_2 \xrightarrow{\text{Oxidase}} P + H_2O_2 \quad (1)$$

$H_2O_2$ is reduced by the immobilized peroxidase:

$$E + H_2O_2 \rightarrow E_1 + H_2O \quad (2)$$

Compound I ($E_1$) is reduced by electron transfer without mediator to the active site of the enzyme:

$$E_1 + e \rightarrow E_2 \quad (3)$$

$$E_2 + e \rightarrow E \quad (4)$$

This hypothesis is supported by the fact that the potential of a single-electron transfer from compound I ($E_1$) and compound II ($E_2$) is very close to the steady state potential of the bienzyme electrodes.

In the case of the HRP, reactions (3) and (4) take place slowly. It is therefore necessary to use immobilized, electrochemically active compounds which are oxidized by HRP:

$$2DMFc^\cdot + H_2O_2 + 2H^+ \longrightarrow 2DMFc^+ + 2H_2O \quad (5)$$

$$2TTF^\cdot + H_2O_2 + 2H^+ \longrightarrow 2TTF^+ + 2H_2O \quad (6)$$

$$2TCNQ^- + H_2O_2 + 2H^+ \longrightarrow 2TCNQ + 2H_2O \quad (7)$$

The reactions on the electrodes are:

$$DMFc^+ + e \longrightarrow DMFc \quad (8)$$

$$TTF^+ + e \longrightarrow TTF \quad (9)$$

$$TCNQ + e \longrightarrow TCNQ^- \quad (10)$$

We claim:
1. Enzyme electrode having a bienzyme system, characterized in that the bienzyme system which comprises; fungal peroxidase and one or more oxidase, and is free of mediators.
2. Enzyme electrode according to claim 1 wherein the bienzyme system contains one or more of the foll glucose oxidase, alcohol oxidase, choline oxidase, D-amino-acid oxidase and cholesterol oxidase as oxidase.
3. Enzyme electrode according to claim 1, wherein the peroxidase and the oxidase(s) are immobilized on the electrode.
4. Enzyme electrode according to claim 3, wherein the peroxidase is covalently bonded to the electrode.
5. Enzyme electrode according to claim 1, wherein the conductive electrode material comprises graphite.
6. Enzyme electrode according to claim 1, wherein said electrode is designed in the form of a strip.
7. Enzyme electrode according to claim 1, characterized in that it is provided on a flat support, optionally together with a counterelectrode.
8. Enzyme electrode according to claim 1 wherein the peroxidase is immobilized on the electrode and the oxidase(s) is held in a space which is formed by the electrode with a semipermeable membrane.
9. Enzyme electrode according to claim 1 wherein both the peroxidase and the oxidase(s) and held in a space which is formed by the electrode with semipermeable membrane.

* * * * *